United States Patent [19]

D'Amico

[11] 4,336,060
[45] Jun. 22, 1982

[54] N-SUBSTITUTED BENZOTHIAZOLINES AND BENZOXAZOLINES AND THEIR USE AS HERBICIDES AND PLANT GROWTH REGULANTS

[75] Inventor: John J. D'Amico, Olivette, Mo.
[73] Assignee: Monsanto Company, St. Louis, Mo.
[21] Appl. No.: 139,063
[22] Filed: Apr. 10, 1980

Related U.S. Application Data

[62] Division of Ser. No. 926,470, Jul. 20, 1978, Pat. No. 4,228,292.

[51] Int. Cl.³ .................. A01N 43/76; A01N 43/78
[52] U.S. Cl. .................................. 71/90; 71/88
[58] Field of Search .......................... 71/88, 90, 76

[56] References Cited

U.S. PATENT DOCUMENTS

| | | | |
|---|---|---|---|
| 3,586,691 | 6/1971 | Scott | 260/304 R |
| 4,049,419 | 9/1977 | D'Amico | 71/76 |
| 4,075,216 | 2/1978 | D'Amico | 260/294.8 C |

FOREIGN PATENT DOCUMENTS 48-10182  3/1973  Japan.

*Primary Examiner*—Catherine L. Mills
*Attorney, Agent, or Firm*—Raymond C. Loyer; Howard C. Stanley

[57] ABSTRACT

N-substituted benzothiazolines and benzoxazolines having the formula

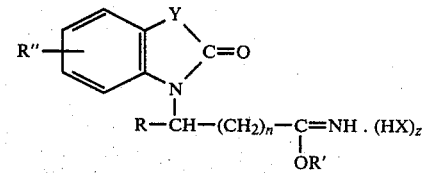

have been found to be effective as herbicides and plant growth regulants.

13 Claims, No Drawings

38° C., 22.8 g (0.2 mole) of 4-chlorobutyronitrile is added in one portion and then heated at 90°–100° C. for 2 days. After cooling to 5° C., 800 grams of ice water is added and stirring continued at 0°–10° C. for 1 hour. The solid is collected by filtration, washed with cold water until neutral to litmus and air-dried at 25°–30° C. The data are summarized in Table II.

sium hydroxide has been replaced by potassium carbonate. To illustrate such a process, Compounds 6 and 7 are prepared as follows.

To a stirred charge containing 0.2 mole of 2-benzothiazolol or 6-bromo-2-benzothiazolol, 28 grams (0.2 mole) of potassium carbonate and 200 ml. of dimethyl formamide, 20.2 grams (0.2 mole) of 97.6% 2-chloro-

TABLE II

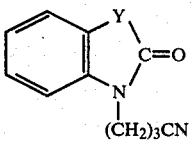

| Compound Number | Y | M.P. °C. | Percent Yield | Percent C Calc'd. | Found | Percent H Calc'd. | Found | Percent N Calc'd. | Found | Percent S Calc'd. | Found |
|---|---|---|---|---|---|---|---|---|---|---|---|
| 4 | S | 61–2[a] | 79 | 60.53 | 60.55 | 4.62 | 4.63 | 12.83 | 12.84 | 14.69 | 14.64 |
| 5 | O | 78–9[b] | 67 | 65.34 | 65.40 | 4.98 | 5.01 | 13.85 | 13.88 | — | — |

[a] Recrystallization from methyl alcohol.
[b] Recrystallization from isopropyl alcohol.

Additionally, it should be noted that compounds in which R is lower alkyl may be prepared in accordance with the above procedure utilizing dimethyl formamide as a solvent in which the alkylnitrile is chlorinated at a different position. For example, if the desired compound is α-methyl-2-oxo-3-benzothiazolinepropionitrile, the alkylnitrile utilized in the procedure above propionitrile is added in one portion and then heated at 80°–90° C. for 24 hours. After cooling to 0° C., 800 grams of ice water is added and stirring continued at 0°–10° C. for one hour. The solid is collected by filtration, washed with water until neutral to litmus and air-dried at 25°–30° C. The data are summarized in Table III.

TABLE III

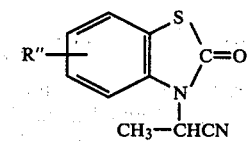

| Compound Number | R" | M.P. °C. | Percent Yield | Percent C Calc'd. | Found | Percent H Calc'd. | Found | Percent N Calc'd. | Found | Percent S Calc'd. | Found |
|---|---|---|---|---|---|---|---|---|---|---|---|
| 6 | H | 107–8[a] | 83 | 58.80 | 58.81 | 3.95 | 3.89 | 13.72 | 13.70 | 15.70 | 15.81 |
| 7 | 6-Br | 170–1[b] | 86 | 42.42 | 42.34 | 2.49 | 2.51 | 9.89 | 9.90 | 11.32 | 11.24 |

[a] Recrystallization from heptane - isopropyl alcohol.
[b] Recrystallization from ethyl acetate.

should be 3-chlorobutyronitrile. If the desired compound is α-methyl-2-oxo-3-benzothiazolinebutyronitrile, the alkylnitrile utilized in the procedure above should be 4-chlorovaleronitrile. As is apparent to those skilled in the art, compounds in which R is to be ethyl, propyl, etc. may be prepared using alkylnitrile chlorinated at a position more closely adjacent to the nitrile moiety.

Preparation of α-methyl-2-oxo-3-benzoxazolineacetonitrile may be accomplished utilizing the above reaction procedure by running the reaction at a somewhat lower temperature, 80°–90° C., for approximately 24 hours.

Nitriles in which R is methyl may also be prepared in a manner similar to the above procedure wherein potas- Another procedure that may be employed for preparing the precursor nitriles where R is hydrogen and n is 1 is the reaction of the appropriate 2-benzothiazolol or 2-benzoxazolol with acrylonitrile in the presence of excess triethylamine wherein Compounds 8–10 may be prepared as follows.

To a stirred solution at 50° C. containing 0.25 mole of 2-benzothiazolol, 6-bromo-2-benzothiazolol or 2-benzoxazolol, 30.4 g (0.3 mole) of triethylamine in 500 ml. of water, 15.9 grams (0.3 mole) of acrylonitrile is added in one portion. The stirred reaction mixture is heated at 50°–60° C. for 6 hours and then at 25°–30° C. for 18 hours. The solid is collected by filtration, washed with water until neutral to litmus and air-dried at 25°–30° C. The data are summarized in Table IV.

N-SUBSTITUTED BENZOTHIAZOLINES AND BENZOXAZOLINES AND THEIR USE AS HERBICIDES AND PLANT GROWTH REGULANTS

This is a division, of application Ser. No. 926,470 filed July 20, 1978, now U.S. Pat. No. 4,228,292.

This invention relates to certain benzothiazoline and benzoxazoline compounds having an imino-ether substituent positioned on the nitrogen atom. The compounds of the invention have been found to be effective agricultural chemicals useful as herbicides as well as plant growth regulants.

The compounds of this invention are imino-ethers derived from 2-oxo-3-benzothiazoline alkyl nitriles and 2-oxo-3-benzoxazoline alkyl nitriles as well as the strong acid salts of said imino-ether compounds and may be represented by the formula

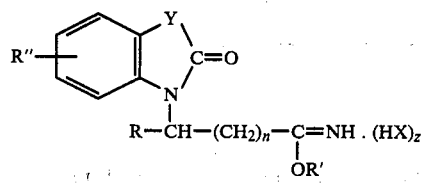

wherein R is hydrogen or lower alkyl, R' is lower alkyl, R" is hydrogen, lower alkyl, halogen or lower alkoxy, Y is oxygen or sulfur, n is an integer from zero to two inclusive, X is an anionic moiety of a strong acid, and z is zero or one.

The term "lower alkyl" or "lower alkoxy" as used herein is understood to include those alkyl or alkoxy groups having up to four carbon atoms, inclusive. Those alkyl and alkoxy groups are meant to include both straight and branched chain.

The term "halogen" as used herein includes chloro, bromo, fluoro and iodo.

The acid salts of the compounds of the foregoing formula are derived from "strong acids" which is understood herein to mean those inorganic and organic acids having a dissociation constant equal to or greater than about $5 \times 10^{-2}$, for example, hydrochloric acid, hydrobromic acid, hydrogen iodide, sulfuric acid, acetic acid, mono-, di- and tri-halogenated acetic acid, oxalic acid, maleic acid and the like. Preferred salts are derived from oxalic acid and the hydrohalic acids, especially hydrochloric acid.

The hydrochloride salts of the imino-ethers of formula (I) may be prepared in accordance with the following reaction scheme:

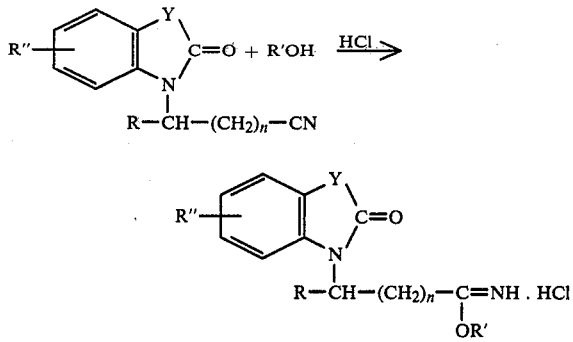

As can be seen from the above reaction, the hydrochloride salts of the imino-ethers may be prepared by addition of HCl gas to the appropriate alcohol and nitrile.

The nitrile precursor may be prepared utilizing a number of procedures depending upon the exact nitrile desired. When R is hydrogen, the nitrile may be prepared in accordance with U.S. Pat. No. 4,049,419 by reaction of the appropriate 2-benzothiazolol or 2-benzoxazolol with potassium hydroxide and chloroalkylnitrile, such as chloroacetonitrile, 3-chloropropionitrile or 4-chlorobutyronitrile. The following examples are presented merely to illustrate the above procedure wherein Compounds 1-3 of Table I may be prepared as follows and are not intended as a limitation on the scope of the invention.

A charge containing 0.2 mole of 6-ethoxy or 6-bromo-2-benzothiazolol or 2-benzoxazolol, 13.2 grams (0.2 mole) of 85% potassium hydroxide and 200 ml. of acetone is stirred for 10 minutes. To the stirred solution at 25° C., 15.4 grams (0.2 mole) of 97% chloroacetonitrile is added in one portion. The stirred reaction mixture is heated at reflux for 6 hours and then at 25°–30° C. for 18 hours. After the addition of 700 ml. of water, stirring is continued for 30 minutes at 25°–30° C. The solid is collected by filtration, washed with water until the washings are neutral to litmus and air-dried at 25°–30° C. The data are summarized in Table I.

TABLE I

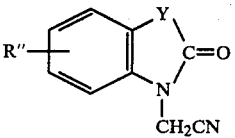

| Compound Number | R" | Y | M.P. °C. | Percent Yield | Percent C Calc'd. | Percent C Found | Percent H Calc'd. | Percent H Found | Percent N Calc'd. | Percent N Found | Percent S Calc'd. | Percent S Found |
|---|---|---|---|---|---|---|---|---|---|---|---|---|
| 1 | 6-OC$_2$H$_5$ | S | 165–6[a] | 92 | 56.40 | 56.18 | 4.30 | 4.28 | 11.96 | 11.92 | 13.69 | 13.77 |
| 2 | 6-Br | S | 186–7[b] | 91 | 40.17 | 40.22 | 1.87 | 1.87 | 10.41 | 10.46 | 11.91 | 11.97 |
| 3 | H | O | 182–3[b] | 95 | — | — | — | — | 16.09 | 16.17 | — | — |

[a]Recrystallization from isopropyl alcohol - ethyl acetate.
[b]Recrystallization from ethyl acetate.

Similarly, Compounds 4 and 5 may be prepared as follows.

A charge containing 0.2 mole of 2-benzothiazolol or 2-benzoxazolol, 13.2 g (0.2 mole) of 85% potassium hydroxide, 200 ml. of dimethyl formamide and 15 ml. of water is stirred for 10 minutes. To the stirred solution at

TABLE IV

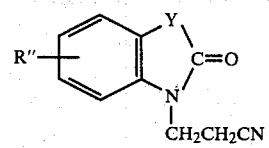

| Compound Number | R'' | Y | M.P. °C. | Percent Yield | Percent C Calc'd. | Percent C Found | Percent H Calc'd. | Percent H Found | Percent N Calc'd. | Percent N Found | Percent S Calc'd. | Percent S Found |
|---|---|---|---|---|---|---|---|---|---|---|---|---|
| 8 | H | S | 116–7[a] | 96 | — | — | — | — | 13.72 | 13.78 | 15.70 | 15.61 |
| 9 | 6-Br | S | 145–6[a] | 92 | 42.42 | 42.52 | 2.49 | 2.51 | 9.89 | 9.86 | 11.32 | 11.28 |
| 10 | H | O | 118–9[b] | 72 | 63.82 | 64.02 | 4.29 | 4.31 | 14.89 | 15.01 | — | — |

[a] Recrystallization from ethyl acetate.
[b] Recrystallization from isopropyl alcohol.

As noted previously, the hydrochloride salt of the imino-ethers of formula (I) may be prepared by addition of HCl gas to the appropriate alcohol and the nitrile precursor. As illustrative thereof, the following procedure is described by which Compounds 11–23 may be prepared.

Hydrogen chloride gas is added at a very slow rate, 0°–10° C., to the appropriate alcohol (methyl, ethyl, propyl, isopropyl, butyl, sec-butyl or tert-butyl) until a 45–50% HCl/alcohol solution is obtained. While stirring this solution which contains from 2.5 to 3.0 moles of HCl in the appropriate alcohol at a temperature of from 0°–20° C., 0.2 moles of the appropriate nitrile precursor is added in one portion. External cooling is removed and stirring is continued for about 3 hours. During this period, a temperature rise from about −20° C. to about 25° C. occurs. After cooling the reaction mixture to about −20° C., 500 to 600 ml. of ethyl ether is added and stirring continued at −20° C. to −15° C. for about 3 minutes. The solid is collected by filtration, washed with 100 ml. of ethyl ether and air-dried at 25°–30° C. Data for Compounds 11–23 are summarized in Table V, below.

TABLE V

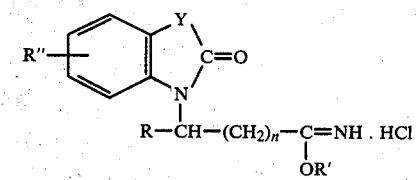

| Compound No. | R'' | Y | R | n | R' | Percent Yield | M.P. °C. | | % C | % H | % Cl | % N | % S |
|---|---|---|---|---|---|---|---|---|---|---|---|---|---|
| 11 | H | S | H | 0 | —CH$_3$ | 79 | 249–50 | Calc'd: | 46.42 | 4.29 | 13.70 | 10.83 | 12.39 |
| | | | | | | | | Found: | 46.20 | 4.32 | 13.82 | 10.85 | 12.35 |
| 12 | H | S | H | 0 | —C$_2$H$_5$ | 76 | 249–50 | Calc'd: | 48.44 | 4.80 | 13.00 | 10.27 | 11.76 |
| | | | | | | | | Found: | 48.32 | 4.99 | 12.54 | 10.01 | 11.56 |
| 13 | H | S | H | 1 | —CH$_3$ | 98 | 193–4 | Calc'd: | 48.44 | 4.80 | 13.00 | 10.27 | 11.76 |
| | | | | | | | | Found: | 48.22 | 4.78 | 12.92 | 10.22 | 11.69 |
| 14* | 5-Cl | S | H | 0 | —CH$_3$ | 95 | 286–8 | Calc'd: | 40.97 | 3.44 | 24.19 | 9.56 | 10.94 |
| | | | | | | | | Found: | 41.06 | 3.46 | 24.11 | 9.54 | 10.88 |
| 15 | 6-OC$_2$H$_5$ | S | H | 0 | —CH$_3$ | 96 | 214–5 | Calc'd: | 47.60 | 4.99 | 11.71 | 9.25 | 10.59 |
| | | | | | | | | Found: | 47.37 | 5.07 | 11.59 | 9.21 | 10.54 |
| 16* | H | S | H | 0 | —CH(CH$_3$)$_2$ | 62 | 224–6 | Calc'd: | 47.29 | 5.62 | 11.63 | 9.19 | 10.52 |
| | | | | | | | | Found: | 48.00 | 5.39 | 11.62 | 9.49 | 10.68 |
| 17 | H | S | H | 0 | —C$_3$H$_7$ | 94 | 241–2 | Calc'd: | — | — | 12.36 | 9.77 | 11.18 |
| | | | | | | | | Found: | — | — | 12.07 | 9.69 | 11.00 |
| 18 | H | S | H | 2 | —CH$_3$ | 90 | 127–8 | Calc'd: | — | — | — | 9.77 | 11.18 |
| | | | | | | | | Found: | — | — | — | 9.89 | 11.03 |
| 19 | H | S | —CH$_3$ | 0 | —CH$_3$ | 95 | 106–8 | Calc'd: | 48.44 | 4.80 | 13.00 | 10.27 | 11.76 |
| | | | | | | | | Found: | 47.80 | 4.74 | 12.65 | 10.24 | 11.57 |
| 20 | 6-Br | S | H | 0 | —CH$_3$ | 99 | 277–8 | Calc'd: | 35.77 | 2.99 | — | 8.30 | 9.50 |
| | | | | | | | | Found: | 35.35 | 2.99 | — | 8.25 | 9.49 |
| 21 | 6-Br | S | —CH$_3$ | 0 | —CH$_3$ | 91 | 202–3 | Calc'd: | 37.57 | 3.44 | — | 7.97 | 9.12 |
| | | | | | | | | Found: | 37.37 | 3.43 | — | 8.00 | 9.06 |
| 22 | H | O | H | 0 | —CH$_3$ | 95 | 252–3 | Calc'd: | 49.50 | 4.57 | 14.61 | 11.54 | — |
| | | | | | | | | Found: | 48.91 | 4.55 | 15.02 | 11.49 | — |
| 23 | 6-Br | S | H | 1 | —CH$_3$ | 98 | 246–7 | Calc'd: | 37.57 | 3.44 | — | 7.97 | 9.12 |
| | | | | | | | | Found: | 37.44 | 3.47 | — | 7.94 | 9.22 |

*In the monohydrate form.

Imino-ethers of formula (I) may be prepared by neutralizing the hydrochloride salt with potassium carbonate in accordance with the following procedure.

To a stirred solution containing 28 grams (0.2 mole) of potassium carbonate in 400 ml. of water, 2 liters of ethyl ether is added. After cooling to 0° C., 0.1 mole of the appropriate imino-ether hydrochloride salt is added in one portion and stirring continued at 0°–10° C. for two hours. The reaction mixture is filtered to remove a small amount of impurities. The separated ethyl ether layer is dried over sodium sulfate and the ether removed in vacuo at a maximum temperature of 60° C. at 1–2 mm. The data are summarized in Table VI.

TABLE VI

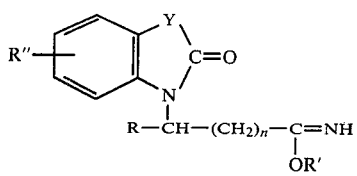

| Compound No. | R" | Y | R | n | R' | Percent Yield | M.P. °C. | | % C | % H | % N | % S |
|---|---|---|---|---|---|---|---|---|---|---|---|---|
| 24 | H | S | H | 0 | —CH$_3$ | 78 | 100–1[a] | Calc'd: | 54.04 | 4.54 | 12.60 | 14.43 |
| | | | | | | | | Found: | 53.71 | 4.57 | 12.53 | 14.36 |
| 25 | H | S | H | 0 | —C$_2$H$_5$ | 64 | 99–100[b] | Calc'd: | 55.91 | 5.12 | 11.86 | 13.57 |
| | | | | | | | | Found: | 55.41 | 5.02 | 11.29 | 14.06 |
| 26 | H | S | H | 1 | —CH$_3$ | 98 | 56–7 | Calc'd: | 55.91 | 5.12 | 11.86 | 13.57 |
| | | | | | | | | Found: | 55.72 | 5.08 | 11.89 | 13.74 |
| 27 | 5-Cl | S | H | 0 | —CH$_3$ | 93 | 125–6[c] | Calc'd: | 46.79 | 3.53 | 10.91 | 12.49 |
| | | | | | | | | Found: | 46.71 | 3.54 | 10.89 | 12.54 |
| 28 | 6-OC$_2$H$_5$ | S | H | 0 | —CH$_3$ | 60 | 115–6[b] | Calc'd: | 54.12 | 5.30 | 10.52 | 12.04 |
| | | | | | | | | Found: | 53.80 | 5.19 | 9.90 | 11.80 |
| 29 | H | S | H | 0 | —CH(CH$_3$)$_2$ | 85 | 46–7 | Calc'd: | 57.58 | 5.64 | — | 12.81 |
| | | | | | | | | Found: | 57.07 | 5.33 | — | 12.69 |
| 30 | H | S | H | 0 | —C$_3$H$_7$ | 94 | 52–3 | Calc'd: | 57.58 | 5.64 | 11.19 | 12.81 |
| | | | | | | | | Found: | 57.00 | 5.36 | 10.67 | 13.12 |
| 31 | H | S | H | 2 | —CH$_3$ | 94 | viscous liquid | Calc'd: | — | — | 11.19 | 12.81 |
| | | | | | | | | Found: | — | — | 10.30 | 13.11 |
| 32 | H | S | —CH$_3$ | 0 | —CH$_3$ | 95 | viscous liquid | Calc'd: | 55.91 | 5.12 | 11.86 | 13.57 |
| | | | | | | | | Found: | 55.70 | 5.13 | 11.79 | 13.72 |
| 33 | 6-Br | S | H | 0 | —CH$_3$ | 95 | 132–3[a] | Calc'd: | 39.88 | 3.01 | 9.30 | 10.65 |
| | | | | | | | | Found: | 39.93 | 3.02 | 9.28 | 10.72 |
| 34 | 6-Br | S | —CH$_3$ | 0 | —CH$_3$ | 92 | 93–4[b] | Calc'd: | 41.92 | 3.52 | 8.89 | 10.17 |
| | | | | | | | | Found: | 42.00 | 3.55 | 8.86 | 10.11 |
| 35 | H | O | H | 0 | —CH$_3$ | 99 | 100–1[b] | Calc'd: | 58.25 | 4.89 | 13.59 | — |
| | | | | | | | | Found: | 58.41 | 5.04 | 13.34 | — |
| 36 | 6-Br | S | H | 1 | —CH$_3$ | 32 | 112–3[b] | Calc'd: | 41.92 | 3.52 | 8.89 | 10.17 |
| | | | | | | | | Found: | 42.08 | 3.73 | 9.01 | 9.81 |

[a] Recrystallization from isopropyl alcohol.
[b] Recrystallization from heptane - isopropyl alcohol.
[c] Recrystallization from methyl alcohol.

Acid salts other than the hydrochloride may be prepared by reaction of the appropriate acid with the imino-ether prepared above. For example, the sulfuric acid salt of Compound 24 may be prepared by adding 7.3 g (0.07 mole) of 95–98% concentrated sulfuric acid to a stirred solution containing 15.6 g (0.07 mole) of Compound 24 and 100 ml. of acetone. After stirring at 25°–30° C. for about 3 hours, the sulfuric acid salt (hereinafter referred to as Compound 37) is collected by filtration and air-dried at 25°–30° C. Compound 37, m.p. 103°–104° C., is obtained in 84% yield.

Anal. Calc'd. for C$_{10}$H$_{10}$N$_2$O$_2$S.H$_2$SO$_4$.2H$_2$O: N, 7.86; S, 17.99. Found: N, 7.79; S, 18.39.

The oxalic acid salt of Compound 24 may be prepared as follows.

To a stirred slurry containing 15.6 g (0.07 mole) of Compound 24 in 200 ml. of ethyl ether, 6.3 g (0.07 mole) of oxalic acid is added in one portion. After stirring at 25°–30° C. for 3 hours, the solid is collected by filtration and air-dried at 25°–30° C. The product (hereinafter referred to as Compound 38), m.p. 160°–163° C. with decomposition, was obtained in 86% yield.

Anal. Calc'd. for C$_{12}$H$_{12}$N$_2$O$_6$S.H$_2$O: N, 8.48; S, 9.71. Found: N, 8.46; S, 9.70.

In accordance with the novel aspects of the present invention, many of the imino-ethers of the foregoing formula (I) have been found to be effective as herbicides. The compounds may be used by themselves or as the active ingredient in a herbicidal composition. More particularly, compounds represented by the following formula have been found to be effective in controlling the growth of undesirable vegetation:

$$\text{(II)}$$

wherein R is hydrogen or lower alkyl; R' is lower alkyl; R" is hydrogen, lower alkyl, halogen or lower alkoxy; Y is oxygen or sulfur; X is an anionic moiety of a strong acid; and z is zero or one. The compounds of the foregoing formula (II) have been found to be especially effective in preventing the growth of broadleaf weeds. Especially effective are those compounds of formula (II) wherein R is hydrogen, R" is hydrogen and Y is sulfur.

As used herein, the term "herbicidal active ingredient" is understood to mean an imino-ether of the foregoing formula (II).

Control of undesirable weed growth may be obtained by applying the herbicidal active ingredient to the plant locus which is defined herein to include the growth medium surrounding the plant, the seeds, emerging seedlings, roots, stems, leaves, flowers and other plant parts. Application to the leaves or stems after the weed has emerged from the soil is preferred. This type of treatment is known to those skilled in the art as a post-emergent treatment.

To illustrate the herbicidal properties of the compounds of the present invention, said compounds were tested in the following manner.

The pre-emergent test was conducted as follows:

A good grade of top soil was placed in aluminum pans and compacted to a depth of 0.95 to 1.27 cm. from the top of the pan. On the top of the soil was placed a predetermined number of seeds or vegetative propagules of various plant species. The soil required to level fill the pans after seeding or adding vegetative propagules was weighed into a pan. A known amount of the herbicidal active ingredient applied in a solvent or as a wettable powder and the soil were thoroughly mixed, and used as a cover layer for prepared pans. After treatment the pans were moved into a greenhouse bench where they were watered from below as needed to give adequate moisture for germination and growth.

As noted in Tables VII and VIII, below, approximately 2 or 4 weeks after seeding and treating, the plants were observed to determine all deviations from the normal growth habit and the results recorded. A herbicidal rating code was used to signify the extent of phytotoxicity of each species. The ratings are defined as follows:

TABLE VII

| Compound Number | WAT* | kg/h | A | B | C | D | E | F | G | H | I | J | K |
|---|---|---|---|---|---|---|---|---|---|---|---|---|---|
| 11 | 4 | 11.2 | 3 | 2 | 3 | 2 | 3 | 2 | 0 | 3 | 0 | 0 | 0 |
| 12 | 4 | 11.2 | 3 | 2 | 3 | 3 | 3 | 3 | 0 | 2 | 0 | 0 | 2 |
| 14 | 4 | 5.6 | 3 | 1 | 1 | 1 | 3 | 1 | 0 | 0 | 0 | 0 | 0 |
| 15 | 2 | 5.6 | 0 | 0 | 0 | 0 | 0 | 0 | 0 | 0 | 0 | 0 | 0 |
| 16 | 4 | 5.6 | 3 | 1 | 1 | 1 | 2 | 1 | 0 | 0 | 0 | 0 | 0 |
| 17 | 4 | 5.6 | 3 | 1 | 1 | 1 | 3 | 2 | 0 | 0 | 0 | 0 | 1 |
| 19 | 2 | 5.6 | 0 | 0 | 0 | 0 | 0 | 0 | 0 | 0 | 0 | 0 | 0 |
| 20 | 2 | 5.6 | 0 | 1 | 0 | 1 | 0 | 0 | 0 | 0 | 0 | 0 | 0 |
| 21 | 2 | 5.6 | 0 | 0 | 0 | 0 | 0 | 0 | 0 | 0 | 0 | 0 | 0 |
| 22 | 2 | 5.6 | 0 | 0 | 0 | 0 | 0 | 0 | 0 | 0 | 0 | 0 | 0 |
| 24 | 4 | 5.6 | 3 | 3 | 2 | 2 | 3 | 2 | 0 | 2 | 0 | 0 | 0 |
| 25 | 4 | 5.6 | 3 | 3 | 2 | 2 | 3 | 3 | 1 | 3 | 2 | 1 | 2 |
| 27 | 2 | 5.6 | 1 | 1 | 1 | 1 | 1 | 1 | 0 | 0 | 0 | 0 | 0 |
| 28 | 2 | 5.6 | 0 | 0 | 0 | 0 | 0 | 0 | 0 | 0 | 0 | 0 | 0 |
| 29 | 4 | 5.6 | 3 | 2 | 2 | 2 | 3 | 2 | 0 | 1 | 0 | 0 | 1 |
| 30 | 4 | 5.6 | 3 | 3 | 2 | 1 | 3 | 2 | 0 | 0 | 0 | 0 | 0 |
| 32 | 2 | 5.6 | 0 | 0 | 0 | 0 | 0 | 0 | 0 | 0 | 0 | 0 | 0 |
| 33 | 4 | 5.6 | 1 | 1 | 1 | 3 | 2 | 1 | 0 | 2 | 0 | 0 | 0 |
| 34 | 4 | 5.6 | 1 | 1 | 0 | 1 | 0 | 0 | 0 | 0 | 0 | 0 | 0 |
| 35 | 2 | 5.6 | 0 | 0 | 0 | 0 | 0 | 0 | 0 | 0 | 0 | 0 | 0 |
| 37 | 2 | 5.6 | 1 | 1 | 1 | 1 | 1 | 0 | 0 | 0 | 0 | 0 | 0 |
| 38 | 4 | 5.6 | 3 | 2 | 1 | 1 | 2 | 1 | 0 | 3 | 0 | 0 | 0 |

*Number of weeks after treatment that observations were made.

TABLE VIII

| Compound Number | WAT* | kg/h | L | M | N | O | P | B | Q | D | R | E | F | C | J | S | K | T |
|---|---|---|---|---|---|---|---|---|---|---|---|---|---|---|---|---|---|---|
| 11 | 4 | 5.6 | 3 | 2 | 1 | 0 | 0 | 2 | 3 | 3 | 3 | 3 | 2 | 3 | 0 | 2 | 1 | 1 |
| 11 | 4 | 1.12 | 2 | 1 | 1 | 0 | 0 | 1 | 1 | 1 | 1 | 1 | 1 | 1 | 0 | 0 | 0 | 0 |
| 12 | 4 | 5.6 | 2 | 3 | 1 | 0 | 0 | 2 | 1 | 1 | 2 | 3 | 2 | 2 | 0 | 0 | 0 | 0 |
| 12 | 4 | 1.12 | 1 | 3 | 0 | 0 | 0 | 1 | 1 | 1 | 1 | 2 | 1 | 1 | 0 | 0 | 0 | 0 |
| 24 | 4 | 5.6 | 3 | 3 | 1 | 1 | 0 | 3 | 3 | 2 | 3 | 3 | 3 | 2 | 0 | 0 | 0 | 1 |
| 24 | 4 | 1.12 | 2 | 1 | 1 | 0 | 0 | 2 | 1 | 1 | 1 | 1 | 1 | 1 | 0 | 0 | 0 | 0 |
| 25 | 4 | 5.6 | 3 | 3 | 1 | 1 | 0 | 3 | 2 | 2 | 3 | 3 | 3 | 3 | 0 | 0 | 0 | 2 |
| 25 | 4 | 1.12 | 2 | 1 | 0 | 0 | 0 | 1 | 1 | 1 | 2 | 2 | 2 | 1 | 0 | 0 | 0 | 0 |
| 25 | 2 | 0.28 | 1 | 1 | 0 | 0 | 0 | 1 | 0 | 0 | 0 | 0 | 0 | 0 | 0 | 0 | 0 | 0 |
| 25 | 2 | 0.056 | 0 | 0 | 0 | 0 | 0 | 1 | 0 | 0 | 0 | 0 | 0 | 0 | 0 | 0 | 0 | 0 |
| 30 | 4 | 5.6 | 3 | 3 | 1 | 1 | 0 | 2 | 2 | 2 | 3 | 3 | 3 | 2 | 0 | 0 | 0 | 3 |
| 30 | 4 | 1.12 | 1 | 1 | 0 | 0 | 0 | 1 | 1 | 1 | 2 | 2 | 1 | 1 | 0 | 0 | 0 | 2 |
| 30 | 2 | 0.28 | 0 | 1 | 0 | 0 | 0 | 1 | 0 | 0 | 1 | 0 | 0 | 0 | 0 | 0 | 0 | 0 |
| 33 | 4 | 5.6 | 1 | 1 | 0 | 0 | 0 | 1 | 1 | 0 | 1 | 1 | — | 0 | 0 | 0 | 0 | 0 |
| 33 | 2 | 1.12 | 0 | 0 | 0 | 0 | 0 | 1 | 0 | 0 | 0 | 0 | 0 | 0 | 0 | 0 | 0 | 0 |
| 33 | 2 | 0.28 | 0 | 0 | 0 | 0 | 0 | 0 | 0 | 0 | 0 | 0 | 0 | — | 0 | 0 | 0 | 0 |

*Number of weeks after treatment that observations were made.

| % Control | Rating |
|---|---|
| 0–24 | 0 |
| 25–49 | 1 |
| 50–74 | 2 |
| 75–100 | 3 |

The plant species utilized in these tests are identified by letter in accordance with the following legend:

| | |
|---|---|
| A - Canada Thistle | K - Barnyard Grass |
| B - Cocklebur | L - Soybean |
| C - Velvetleaf | M - Sugar Beet |
| D - Morning Glory | N - Wheat |
| E - Lambsquarters | O - Rice |
| F - Smartweed | P - Sorghum |
| G - Nutsedge | Q - Wild Buckwheat |
| H - Quackgrass | R - Hemp Sesbania |
| I - Johnson Grass | S - Panicum Spp. |
| J - Downy Brome | T - Crabgrass |

Results of the pre-emergent tests are summarized in Tables VII and VIII, below.

The post-emergent tests were conducted as follows:

The herbicidal active ingredients are applied in spray form to two or three-week old specimens of various plant species. The spray, a solution or wettable powder suspension containing the appropriate rate of herbicidal active ingredient to give the desired test rate and a surfactant, is applied to the plants. The treated plants are placed in a greenhouse and approximately two or four weeks later the effects are observed and recorded. The results are shown in Tables IX and X in which the post-emergent herbicidal rating code is as follows:

| % Control | Rating |
|---|---|
| 0–24 | 0 |
| 25–49 | 1 |
| 50–74 | 2 |
| 75–99 | 3 |
| 100 | 4 |

The plant species utilized in these tests are identified by letter in accordance with the previous legend.

TABLE IX

| Compound Number | WAT* | kg/h | A | B | C | D | E | F | G | H | I | J | K |
|---|---|---|---|---|---|---|---|---|---|---|---|---|---|
| 11 | 4 | 11.2 | 3 | 3 | 2 | 2 | 4 | 4 | 0 | 0 | 0 | 0 | 1 |
| 11 | 4 | 5.6 | 4 | 3 | 3 | 2 | 4 | 4 | 0 | 0 | 1 | 0 | 0 |
| 12 | 4 | 11.2 | 2 | 3 | 3 | 2 | 4 | 4 | 0 | 2 | 0 | 0 | 1 |
| 14 | 4 | 5.6 | 2 | 1 | 1 | 2 | 3 | 1 | 0 | 0 | 0 | 0 | 0 |
| 15 | 2 | 5.6 | 0 | 1 | 0 | 0 | 1 | 0 | 0 | 0 | 0 | 0 | 0 |
| 16 | 4 | 5.6 | 2 | 2 | 2 | 2 | 4 | 2 | 0 | 0 | 0 | 0 | 0 |
| 17 | 4 | 5.6 | 2 | 2 | 2 | 2 | 4 | 2 | 0 | 0 | 0 | 0 | 0 |
| 19 | 2 | 11.2 | 1 | 1 | 1 | 1 | 1 | 0 | 0 | 0 | 0 | 0 | 0 |
| 20 | 4 | 5.6 | 1 | 1 | 1 | 1 | 2 | 1 | 0 | 0 | 0 | 0 | 0 |
| 21 | 2 | 5.6 | 0 | 1 | 0 | 1 | 1 | 0 | 0 | 0 | 0 | 0 | 0 |
| 22 | 2 | 5.6 | 0 | 1 | 0 | 1 | 0 | 0 | 0 | 0 | 0 | 0 | 0 |
| 24 | 4 | 5.6 | — | 4 | 3 | 2 | 4 | 4 | 0 | 0 | 1 | 1 | 1 |
| 25 | 4 | 5.6 | 4 | 3 | 2 | 2 | 4 | 4 | 0 | 0 | 0 | 0 | 0 |
| 27 | 4 | 5.6 | 4 | 3 | 2 | 2 | 4 | 4 | 0 | 0 | 0 | 0 | 0 |
| 28 | 2 | 5.6 | 0 | 1 | 0 | 0 | 0 | 0 | 0 | 0 | 0 | 0 | 0 |
| 29 | 4 | 5.6 | 2 | 2 | 2 | 2 | 4 | 2 | 0 | 0 | 0 | 0 | 0 |
| 30 | 4 | 5.6 | 3 | 2 | 2 | 2 | 4 | 3 | 0 | 0 | 0 | 0 | 0 |
| 32 | 4 | 11.2 | 1 | 1 | 1 | 1 | 3 | 2 | 0 | 0 | 0 | 0 | 0 |
| 33 | 4 | 5.6 | 2 | 2 | 1 | 2 | 3 | 2 | 0 | 1 | 0 | 0 | 1 |
| 34 | 4 | 5.6 | 4 | 2 | 1 | 2 | 4 | 0 | 0 | 0 | 0 | 0 | 0 |
| 35 | 2 | 5.6 | 0 | 0 | 0 | 1 | 0 | 0 | 0 | 0 | 0 | 0 | 1 |
| 37 | 4 | 5.6 | 2 | 3 | 2 | 2 | 4 | 4 | 0 | 0 | 0 | 0 | 0 |
| 38 | 4 | 5.6 | 3 | 3 | 2 | 2 | 4 | 3 | 0 | 0 | 0 | 0 | 0 |

*Number of weeks after treatment that observations were made.

TABLE X

| Compound Number | WAT* | kg/h | L | M | N | O | P | B | Q | D | R | E | F | C | J | S | K | T |
|---|---|---|---|---|---|---|---|---|---|---|---|---|---|---|---|---|---|---|
| 11 | 4 | 5.6 | 3 | 4 | 1 | 0 | 1 | 4 | 4 | 2 | 3 | 4 | 4 | 3 | 1 | 1 | 1 | 0 |
| 11 | 4 | 1.12 | 1 | 2 | 1 | 0 | 0 | 2 | 2 | 2 | 1 | 4 | 1 | 1 | 0 | 0 | 0 | 0 |
| 12 | 4 | 5.6 | 2 | 3 | 1 | 0 | 0 | 3 | 3 | 2 | 3 | 4 | 4 | 3 | 0 | 0 | 0 | 0 |
| 12 | 4 | 1.12 | 1 | 2 | 0 | 0 | 0 | 2 | 2 | 2 | 2 | 4 | 4 | 2 | 0 | 0 | 0 | 0 |
| 12 | 4 | 0.28 | 1 | 1 | 0 | 0 | 0 | 1 | 1 | 1 | 1 | 2 | 2 | 1 | 0 | 0 | 0 | 0 |
| 24 | 4 | 5.6 | 2 | 3 | 1 | 0 | 1 | 4 | 4 | 3 | 4 | 4 | 4 | 4 | 2 | 0 | 0 | 0 |
| 24 | 4 | 1.12 | 2 | 2 | 0 | 1 | 1 | 4 | 4 | 2 | 2 | 4 | 3 | 2 | 0 | 0 | 0 | 0 |
| 24 | 4 | 0.28 | 1 | 1 | 0 | 0 | 0 | 2 | 1 | 2 | 1 | 2 | 1 | 2 | 0 | 0 | 0 | 0 |
| 24 | 2 | 0.056 | 1 | 1 | 0 | 0 | 0 | 1 | 1 | 1 | 0 | 1 | 0 | 1 | 0 | 0 | 0 | 0 |
| 27 | 4 | 5.6 | 3 | 3 | 1 | 0 | 0 | 3 | 4 | 2 | 4 | 4 | 4 | 2 | 0 | 0 | 0 | 0 |
| 27 | 4 | 1.12 | 2 | 3 | 0 | 0 | 0 | 2 | 3 | 2 | 2 | 3 | 3 | 2 | 0 | 0 | 0 | 0 |
| 27 | 2 | 0.28 | 1 | 1 | 0 | 0 | 0 | 1 | 0 | 1 | 0 | 1 | 0 | 1 | 0 | 0 | 0 | 0 |
| 37 | 4 | 5.6 | 2 | 2 | 0 | 0 | 0 | 3 | 4 | 3 | 3 | 4 | 4 | — | 0 | 0 | 1 | 1 |
| 37 | 4 | 1.12 | 1 | 2 | 0 | 0 | 0 | 2 | 2 | 2 | 2 | 4 | 2 | — | 0 | 0 | 0 | 0 |
| 38 | 4 | 1.12 | 1 | 2 | 0 | 1 | 0 | 3 | 2 | 2 | 1 | 3 | 3 | 1 | 0 | 0 | 0 | 0 |
| 38 | 2 | 0.28 | 1 | 1 | 0 | 0 | 0 | 1 | 0 | 1 | 0 | 1 | 0 | 1 | 0 | 0 | 0 | 0 |

*Number of weeks after treatment that observations were made.

From the above data it is apparent that the compounds of formula (II) are especially effective in controlling the growth of undesirable broadleaf weeds, especially when applied as a post-emergent. The data also indicates that the compounds are somewhat selective to narrowleaf crops such as wheat, rice and sorghum. In other words, application of the compounds of formula (II) to the locus of narrowleaf crop plants such as wheat, rice and sorghum, especially sorghum, results in the prevention of weeds, especially broadleaf weeds, while the narrowleaf crop remains unharmed.

The above tables illustrate one aspect of the present invention, that is, the use of the compounds of the invention to kill or injure undesirable plants, e.g., weeds. Another aspect of the invention, however, is the use of many of the imino-ethers of formula (I) for the regulation of desirable plant growth, especially leguminous plants such as soybeans. More particularly, compounds represented by the following formula have been found to be effective in regulating the growth of leguminous plants:

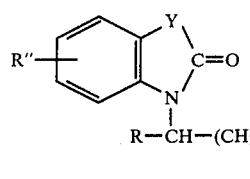

$$R''-\underset{}{\underset{}{\bigcirc}}\overset{Y}{\underset{N}{\diagdown}}C=O$$

$$R-CH-(CH_2)_n-CH=NH \cdot (HX)_z$$
$$\underset{OR'}{|}$$

(III)

wherein R is hydrogen or lower alkyl; R' is lower alkyl; R'' is hydrogen, lower alkyl or halogen; Y is oxygen or sulfur; X is an anionic moiety of a strong acid; n is an integer from zero to three, inclusive; and z is zero or one.

As used herein, the regulation of "plant growth or development" is understood to mean the modification of the normal sequential development of a treated desirable plant to agricultural maturity. Such modifications are most readily observed as changes in size, shape, color or texture of the treated plant or any of its parts. Similarly, changes in the quantity of plant fruit or flowers are also quite apparent from visual inspection. The above changes may be characterized as an acceleration or retardation of plant growth, stature reduction, leaf or canopy alteration, increased branching, terminal inhibition, increased flowering, defoliation, increased root growth, increased cold hardiness and the like. While many of these modifications are desirable in and of themselves, most often it is their effect on the economic result that is of most importance. For example, a reduction in stature of the plant permits the growing of more plants per unit area. A darkening of the foliar color may be illustrative of higher chlorophyll activity indicative of improved rate of photosynthesis.

Although the regulation of plant growth in accordance with the present invention may include partial inhibition of plant growth when used as a plant growth regulant, it does not include the total inhibition or killing of such plants. The present invention contemplates the use of an amount of the imino-ether of formula (III) as the active ingredient in a plant growth regulating composition which will modify the normal sequential development of the treated plant to agricultural maturity. Such plant growth regulating amounts may vary, not only with the material selected, but also with the modifying effect desired, the species of plant and its stage of development, the plant growth medium and whether a permanent or a transitory effect is sought. It is, however, well within the skill of the art to determine the amount of active ingredient required.

Modification of the plants may be accomplished by applying the active ingredient to the plant locus which has been defined herein to include the growth medium surrounding the plant, the seeds, emerging seedlings, roots, stems, leaves, flowers, or other plant parts. Such application may be made directly to the plant part, or indirectly by application to the plant growth medium.

Utilizing the imino-ether of formula (III) as the active ingredient in a plant growth regulating composition, said compounds were found to possess plant growth regulating activity when tested in accordance with the following procedure.

A number of soybean plants, variety Williams, were grown from seeds in plastic pots in the greenhouse for a period of one week at which time the plants are thinned to one plant per pot. When the second trifoliate leaf (three weeks) was fully expanded, the plants were treated with a solution of the active ingredient in acetone and water. Aqueous Tween 20 was used as a surfactant.

When the fifth trifoliate leaf (four to five weeks) was fully expanded, the treated plants were compared with the non-treated control plants and the observations recorded. Those observations are summarized in Table XI, below.

TABLE XI

| Compound Number | Rate (kg/h) | Observations |
|---|---|---|
| 11 | 2.8 | Stature reduction, stem distortion, leaf distortion, altered canopy, inhibition of apical development, inhibition of dry weight, moderate leaf burn. |
| 11 | 0.56 | Stature reduction, stem distortion, leaf distortion, altered canopy, inhibition of apical development, inhibition of dry weight, slight leaf burn. |
| 11 | 0.112 | Stem distortion, leaf distortion, altered canopy, inhibition of apical development, inhibition of dry weight, slight leaf burn. |
| 12 | 2.8 | Altered canopy, epinasty, leaf distortion, leaf distortion of new growth, inhibition of apical development, inhibition of dry weight, slight leaf burn. |
| 12 | 0.56 | Stature reduction, stem distortion, leaf alteration of new growth, leaf inhibition, altered canopy, inhibition of dry weight. |
| 12 | 0.112 | Inhibition of axillary buds, altered canopy, leaf alteration of new growth, leaf inhibition, inhibition of dry weight. |
| 14 | 2.8 | Stature reduction, stem distortion, leaf distortion, leaf inhibition, selective apical kill, inhibition of dry weight, severe leaf burn. |
| 14 | 0.56 | Altered canopy, leaf alteration, leaf distortion, leaf inhibition, inhibition of apical development, inhibition of dry weight, slight leaf burn. |
| 14 | 0.112 | Altered canopy, leaf alteration of new growth, leaf inhibition, inhibition of dry weight, slight leaf burn. |
| 16 | 2.8 | Stature reduction, leaf distortion, leaf inhibition, epinasty, inhibition of apical development, inhibition of dry weight, moderate leaf burn. |
| 16 | 0.56 | Stature reduction, altered canopy, stem distortion, leaf alteration, leaf inhibition, inhibition of dry weight, slight leaf burn. |
| 16 | 0.112 | Altered canopy, leaf alteration, leaf inhibition, stem distortion, inhibition of dry weight. |
| 17 | 2.8 | Stature reduction, epinasty, leaf distortion, leaf inhibition, inhibition of apical development, inhibition of dry weight, slight leaf burn. |
| 17 | 0.56 | Altered canopy, leaf alteration, leaf inhibition, stem distortion, inhibition of apical development, inhibition of dry weight. |
| 17 | 0.112 | Altered canopy, leaf alteration, leaf inhibition, stem distortion, inhibition of dry weight. |
| 18 | 2.8 | Altered canopy, leaf distortion, leaf inhibition, slight leaf burn. |
| 18 | 0.56 | No response. |
| 18 | 0.112 | No response. |
| 20 | 2.8 | Altered canopy, leaf alteration, leaf inhibition, stem distortion, inhibition of apical development, inhibition of dry weight. |
| 20 | 0.56 | Altered canopy, leaf alteration of new growth, leaf inhibition, inhibition of dry weight. |
| 20 | 0.112 | Leaf alteration of new growth. |
| 22 | 2.8 | Altered canopy, leaf alteration of new growth, leaf inhibition, inhibition of dry weight. |
| 22 | 0.56 | Leaf alteration of new growth. |
| 22 | 0.112 | Leaf alteration of new growth, inhibition of dry weight. |
| 24 | 2.8 | Stature reduction, altered canopy, stem distortion, leaf distortion, inhibition of apical development, inhibition of dry weight, moderate leaf burn. |
| 24 | 0.56 | Stature reduction, altered canopy, stem distortion, leaf distortion, inhibition of apical development, inhibition of dry weight, slight leaf burn. |
| 24 | 0.112 | Stature reduction, altered canopy, stem distortion, leaf alteration, inhibition of apical development, inhibition of dry weight, slight leaf burn. |
| 25 | 2.8 | Stature reduction, chlorosis, epinasty, leaf distortion, inhibition of apical development, inhibition of dry weight, slight leaf burn. |
| 25 | 0.56 | Stature reduction, chlorosis, stem distortion, leaf alteration, inhibition of apical development, inhibition of dry weight. |
| 25 | 0.112 | Stature reduction, chlorosis, stem distortion, leaf alteration, inhibition of apical development, inhibition of dry weight. |
| 26 | 2.8 | Altered canopy, leaf alteration of new growth, leaf inhibition. |
| 26 | 0.56 | Leaf alteration of new growth, leaf inhibition, inhibition of dry weight. |
| 26 | 0.112 | Leaf alteration of new growth, leaf inhibition, inhibition of dry weight. |
| 27 | 2.8 | Plants died. |
| 27 | 0.56 | Stature reduction, stem distortion, leaf distortion, leaf inhibition, selective apical kill, inhibition of dry weight, moderate leaf burn. |
| 27 | 0.112 | Altered canopy, leaf alteration, leaf inhibition, inhibition of dry weight, slight leaf burn. |
| 29 | 2.8 | Stature reduction, epinasty, leaf distortion, leaf inhibition, inhibition of apical development, inhibition of dry weight, slight leaf burn. |
| 29 | 0.56 | Stature reduction, stem distortion, leaf |

TABLE XI-continued

| Compound Number | Rate (kg/h) | Observations |
|---|---|---|
| | | alteration, leaf inhibition, altered canopy, slight leaf burn, inhibition of dry weight. |
| 29 | 0.112 | Altered canopy, stem distortion, leaf alteration, leaf inhibition, inhibition of dry weight. |
| 30 | 2.8 | Stature reduction, epinasty, leaf distortion, leaf inhibition, inhibition of apical development, inhibition of dry weight, slight leaf burn. |
| 30 | 0.56 | Altered canopy, stem distortion, leaf alteration, leaf inhibition, inhibition of apical development, inhibition of dry weight. |
| 30 | 0.112 | Altered canopy, leaf alteration, leaf inhibition, inhibition of dry weight. |
| 31 | 2.8 | Altered canopy, leaf alteration of new growth, leaf inhibition, slight leaf burn. |
| 31 | 0.56 | Leaf alteration of new growth, leaf inhibition, inhibition of dry weight. |
| 31 | 0.112 | Leaf alteration of new growth, inhibition of dry weight. |
| 32 | 2.8 | Stature reduction, leaf alteration of new growth, epinasty, leaf distortion, leaf inhibition, inhibition of dry weight, slight leaf burn. |
| 32 | 0.56 | Stature reduction, leaf alteration of new growth, stem distortion, leaf distortion, leaf inhibition, inhibition of dry weight, slight leaf burn. |
| 32 | 0.112 | Inhibition of dry weight. |
| 33 | 2.8 | Stature reduction, epinasty, leaf distortion, leaf inhibition, inhibition of apical development, inhibition of dry weight, slight leaf burn. |
| 33 | 0.56 | Stature reduction, stem distortion, leaf alteration, leaf inhibition, inhibition of apical development, inhibition of dry weight. |
| 33 | 0.112 | Inhibition of dry weight. |
| 34 | 2.8 | Stature reduction, epinasty, stem distortion, leaf distortion of new growth, inhibition of apical development, inhibition of dry weight, slight leaf burn. |
| 34 | 0.56 | Stature reduction, stem distortion, leaf inhibition, inhibition of apical development, inhibition of dry weight. |
| 34 | 0.112 | Leaf alteration of new growth. |
| 35 | 2.8 | Leaf alteration of new growth, slight leaf burn. |
| 35 | 0.56 | No response. |
| 35 | 0.112 | No response. |
| 36 | 2.8 | Altered canopy, leaf distortion of old and new growth, leaf alteration of new growth, slight leaf burn. |
| 36 | 0.56 | Leaf alteration of new growth. |
| 36 | 0.112 | Leaf alteration of new growth. |
| 37 | 2.8 | Leaf alteration of old and new growth, epinasty, leaf inhibition, inhibition of apical development, inhibition of dry weight. |
| 37 | 0.56 | Stature reduction, altered canopy, stem distortion, leaf alteration of new growth, leaf inhibition, inhibition of dry weight. |
| 37 | 0.112 | Altered canopy, leaf alteration of new growth, leaf inhibition, axillary bud inhibition, inhibition of dry weight. |
| 38 | 2.8 | Stature reduction, epinasty, leaf distortion, leaf inhibition, inhibition of apical development, inhibition of dry weight, slight leaf burn. |
| 38 | 0.56 | Stature reduction, leaf alteration, stem distortion, leaf inhibition, inhibition of apical development, inhibition of dry weight. |
| 38 | 0.112 | Altered canopy, leaf alteration, stem distortion, leaf inhibition, inhibition of apical development, inhibition of dry weight. |

As can be seen from the above data, the imino-ethers of formula (III) above are especially effective at rates of about 2.8 kilograms per hectare in reducing the stature of soybean plants. At lower rates, the compounds are effective in altering the leaf morphology of the plant without reducing the plant's stature.

Thus, the above data illustrate that the compounds of the invention may be used as a herbicide or a plant growth regulant. When used as a herbicide, it is desirable that rates of application about 1.12 kilograms per hectare and above be utilized. When used to regulate the growth of desirable plants, rates below 5.6 kilograms per hectare, especially 0.056 to 2.8, are preferred.

In selecting the appropriate time and rate of application of the active ingredient, it will be recognized that precise rates will also be dependent upon the desired response, mode of application, plant variety, soil conditions and various other factors known to those skilled in the art. In addition, it will be recognized that single or multiple applications may be used to exert the desired response.

In the practice of the invention, the active ingredient, whether used as a herbicide or a plant growth regulant, can be used alone or in combination with other pesticides or a material referred to in the art as an adjuvant in either liquid or solid form. To prepare such compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, power dusters, boom and hand sprayers and spray dusters. The composition can also be applied from airplanes as a dust or spray.

Compositions of this invention, whether used as a herbicide or a plant growth regulant, generally contain from about 5 to 95 parts active ingredient, about 1 to 50 parts surface-active agent and about 4 to 94 parts solvents, all parts being by weight based on the total weight of the composition.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of regulating the growth of desirable plants which comprises applying to the plant locus a plant growth regulating effective amount of a compound having the formula

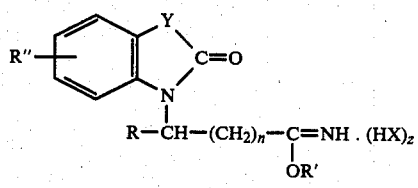

wherein R is hydrogen or lower alkyl; R' is lower alkyl; R" is hydrogen, lower alkyl or halogen; Y is oxygen or sulfur; X is an anionic moiety of a strong acid, n is an integer from zero to two, inclusive and z is zero or one.

2. A method according to claim 1 wherein Y is sulfur.

3. A method according to claim 2 wherein R is hydrogen.

4. A method according to claim 1 wherein z is zero.

5. A method according to claim 1 wherein z is one.

6. A method according to claim 5 wherein X is chloro.

7. An agricultural chemical composition which comprises from about 5 to about 95 parts by weight of a compound having the formula

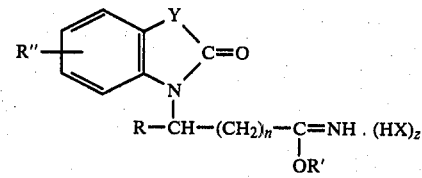

wherein R is hydrogen or lower alkyl; R' is lower alkyl; R" is hydrogen, lower alkyl, halogen or lower alkoxy; Y is oxygen or sulfur; n is an integer from zero to two inclusive; X is an anionic moiety of a strong acid and z is zero or one; the remaining parts being comprised of one or more suitable adjuvants, carriers and/or diluents.

8. A composition according to claim 7 wherein n is zero.

9. A composition according to claim 7 wherein R is hydrogen.

10. A composition according to claim 7 wherein R is hydrogen, R' is hydrogen and Y is sulfur.

11. A composition according to claim 7 wherein z is zero.

12. A composition according to claim 7 wherein z is one.

13. A composition according to claim 12 wherein X is chloro.

* * * * *